US007703313B2

(12) United States Patent
Higashi

(10) Patent No.: US 7,703,313 B2
(45) Date of Patent: Apr. 27, 2010

(54) CONFORMAL FILM MICRO-CHANNELS FOR A FLUIDIC MICRO ANALYZER

(75) Inventor: Robert E. Higashi, Shorewood, MN (US)

(73) Assignee: Honeywell International Inc., Morristown, NJ (US)

( * ) Notice: Subject to any disclaimer, the term of this patent is extended or adjusted under 35 U.S.C. 154(b) by 303 days.

(21) Appl. No.: 11/675,043

(22) Filed: Feb. 14, 2007

(65) Prior Publication Data

US 2008/0190171 A1    Aug. 14, 2008

(51) Int. Cl.
 *G01N 25/00* (2006.01)
(52) U.S. Cl. .................... 73/25.01; 422/68.1; 216/2
(58) Field of Classification Search ............ 216/2; 422/68.1; 73/25.01, 25.03, 23.4, 23.35
 See application file for complete search history.

(56) References Cited

U.S. PATENT DOCUMENTS

| 6,036,872 | A  | * | 3/2000  | Wood et al. ............... 216/2   |
| 6,093,330 | A  |   | 7/2000  | Chong                              |
| 6,096,656 | A  |   | 8/2000  | Matzke et al.                      |
| 6,322,247 | B1 | * | 11/2001 | Bonne et al. ............. 374/138  |
| 6,359,333 | B1 | * | 3/2002  | Wood et al. .............. 257/704  |
| 6,393,894 | B1 | * | 5/2002  | Bonne et al. ............. 73/23.2  |
| 7,000,452 | B2 | * | 2/2006  | Bonne et al. ............ 73/23.25  |
| RE39,143  | E  | * | 6/2006  | Wood et al. ............... 216/2   |
| 7,549,206 | B2 | * | 6/2009  | Higashi et al. .......... 29/592.1  |
| 2004/0129057 | A1 | * | 7/2004 | Bonne et al. ............ 73/25.03 |
| 2005/0063865 | A1 |   | 3/2005 | Bonne et al.                       |

FOREIGN PATENT DOCUMENTS

EP    1178309 A1    2/2002

OTHER PUBLICATIONS de Boer, M.J.; Tjerkstra, R.W.; Berenschot, J.W.; Jansen, H.V.; Burger, G.J.; Gardeniers, J.G.E.; Elwenspoek, M.; van den Berg, A., "Micromachining of buried micro channels in silicon," Microelectromechanical Systems, Journal of , vol. 9, No. 1, pp. 94-103, Mar. 2000.*
Dijkstra, M.; de Boer, M.J.; Berenschot, M.J.W.; Lammerink, T.S.J.; Wiegerink, R.J.; Elwenspoek, M., "Miniaturized flow sensor with planar integrated sensor structures on semicircular surface channels," Micro Electro Mechanical Systems, 2007. MEMS. IEEE 20th International Conference on, pp. 123-126, Jan. 21-25, 2007.*

* cited by examiner

*Primary Examiner*—Lisa M Caputo
*Assistant Examiner*—Punam Patel
(74) *Attorney, Agent, or Firm*—Schwegman, Lundberg & Woessner, P.A.

(57) ABSTRACT

Embodiments of the invention relate to a fluid containment structure for a micro analyzer comprising one or more shelled thermal structures in contact with a thermally isolated component of the analyzer and wherein the shelled thermal structure comprises a conformal film and also comprises three walls of a channel and the thermally isolated component forms the fourth wall.

4 Claims, 10 Drawing Sheets

CONFORMAL FILM MICRO-CHANNELS FOR A FLUIDIC MICRO ANALYZER

TECHNICAL FIELD

Embodiments of the present invention relate to shelled thermal structures for fluid sensing. More specifically, embodiments of the present invention relate to shelled thermal structures for a micro or MEMS (Micro-Electro-Mechanical System) gas chromatograph.

BACKGROUND

Multi-fluid detection and analysis may be automated via affordable, in-situ, ultra-sensitive micro sensors and analyzers, such as a micro gas chromatograph. A large portion or all of a micro gas chromatograph (GC) may be integrated on a chip with conventional semiconductor processes or micro electro-mechanical system (MEMS) techniques. GC-MEMS sensors may include concentrator and separator components to enhance the detection of gases and vapors at low concentrations. Such detection is often difficult due to limitations in the sensitivity of detector devices and measurement instruments. The process of detecting various constituents within a gas sample at low concentrations can be greatly enhanced if the constituents can be concentrated prior to detection.

The current method for making a GC-MEMS requires significant power consumption to heat the active surface as well as any passive surfaces in close proximity. Gas containment in the system is normally accomplished using silicon or some other film attached to the silicon as containment. Theses surfaces act as a heat sink and require significant amounts of power to maintain the thermally isolated component of the device at a given temperature.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

SUMMARY

Figure 1A:
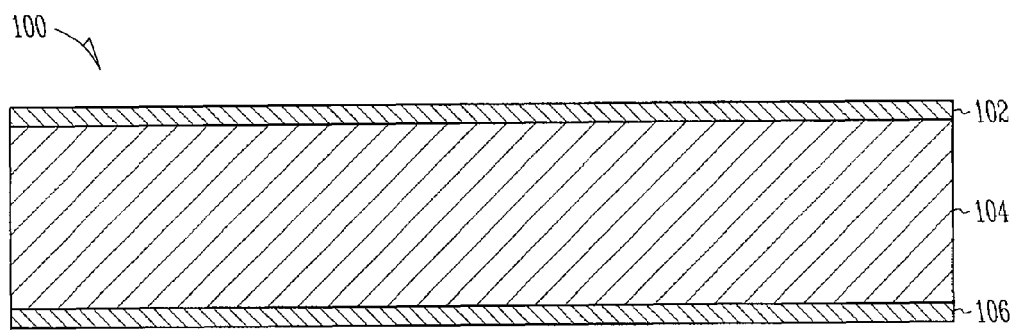
FIGS. 1A-1R illustrate a cross-sectional view of steps in a method of making a shelled thermal structure for fluid sensing, according to some embodiments.

Embodiments of the present invention relate to a fluid containment structure for a micro analyzer comprising one or more shelled thermal structures in contact with a thermally isolated component of the analyzer and wherein the shelled thermal structure comprises a conformal film and also comprises three walls of a channel and the thermally isolated component forms the fourth wall.

Embodiments also relate to a fluidic micro analyzer, comprising drive electronics, heating elements thermally isolated from other micro analyzer components and in electrical contact with the drive electronics. The analyzer also includes one or more shelled thermal structures in contact with the heating elements, monitoring sensors in electrical contact with the drive electronics, a fluidic channel, a fluid inlet for introducing a fluidic sample to the channel, a fluid exit and one or more detectors positioned in the fluidic channel or near the fluid inlet or exit. The one or more shelled thermal structures comprise three walls of at least a portion of the channel and the heating elements form the fourth wall of at least a portion of the channel.

Embodiments of the present invention also relate to a method of making a shelled thermal structure for a micro analyzer comprising forming micro analyzer structures on a wafer, depositing insulator layer on structures, depositing coating on one or more structures and forming shelled thermal structures on the insulator layer.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Embodiments of the invention relate to a shelled thermal structure for use with a micro fluid detection system, such as a GC-MEMS. The shelled thermal structure allows for a thin shell to contain fluid and be attached to a thermally isolated component, such as a thermally isolated diaphragm. The diaphragm may include heating elements and form one wall of a four wall channel. The shelled thermal structure may then form the other three walls and be attached to the diaphragm. By not attaching directly to a silicon heat sink, the overall power consumption is significantly reduced. Examples of diaphragms, concentrators, separators and micro fluid analyzers may be found in commonly owned U.S. Pat. Nos. 6,393,894; 7,000,452; 6,036,872; 6,359,333; RE39,143; 6,322,247; the disclosures of which are incorporated herein in their entirety.

In addition, the amount of thermal isolation can be controlled externally to the fluid containment, unlike conventional systems which compromise between the active surface and isolation as the isolation mechanism is internal to the containment. In the fabrication process, the number of wafers and number of seals is also reduced, allowing for simplification and greater reliability.

The shelled thermal structures of the present invention may be utilized in fluid separation, fluid concentration or both in a GC-MEMS, for example. The shelled thermal structures may create thermally isolated channels that may be loaded with a chemical that could be driven off thermally to be used as a micro calibration source.

Figure 1B:
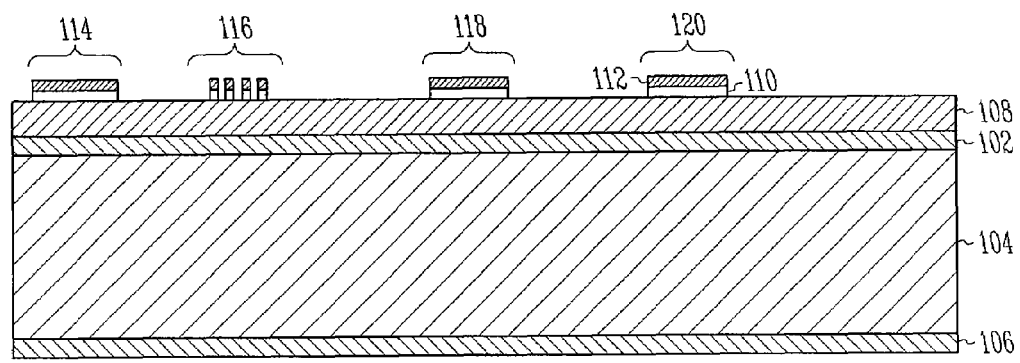
Figure 1C:
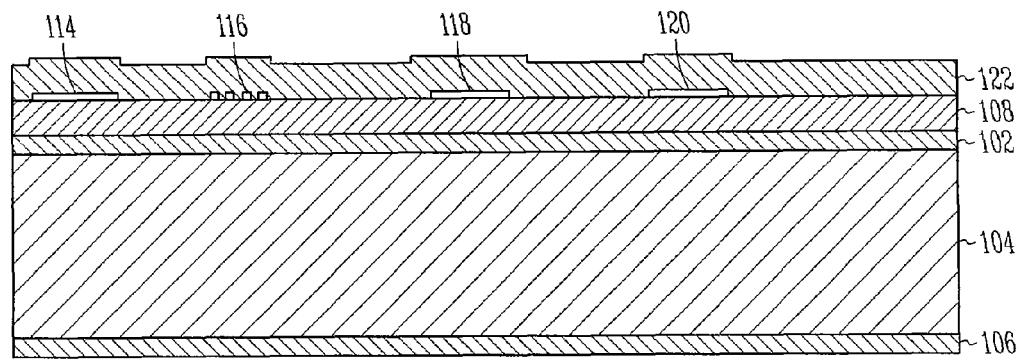
Figure 1D:
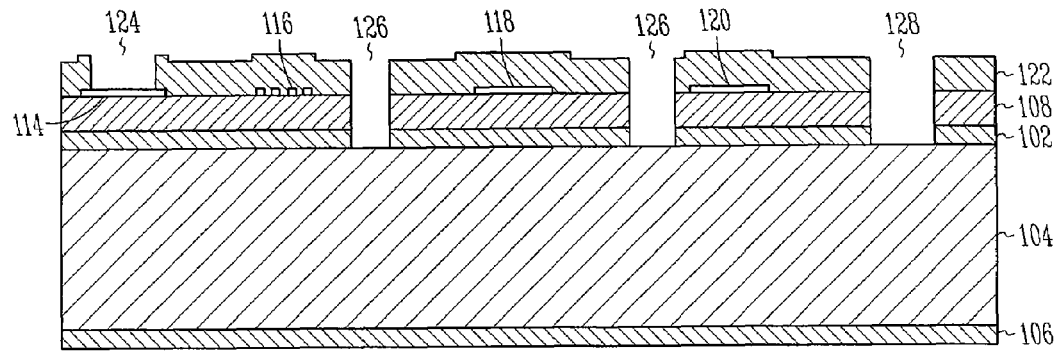
Figure 1E:
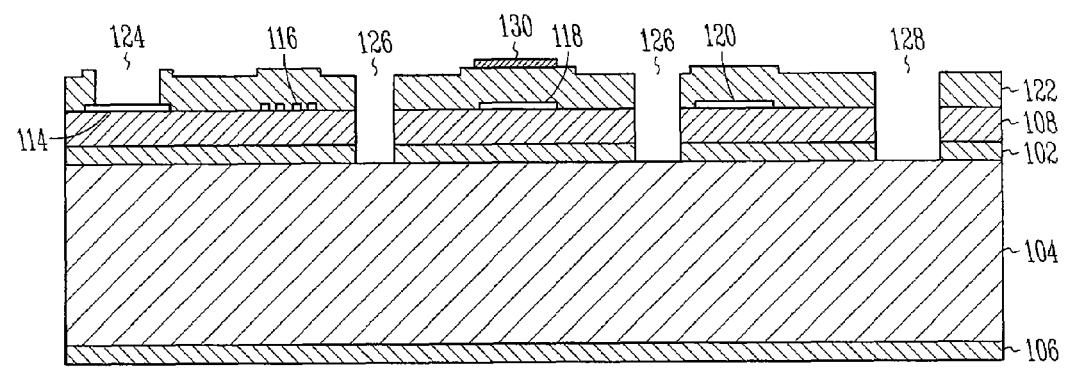
Figure 1F:
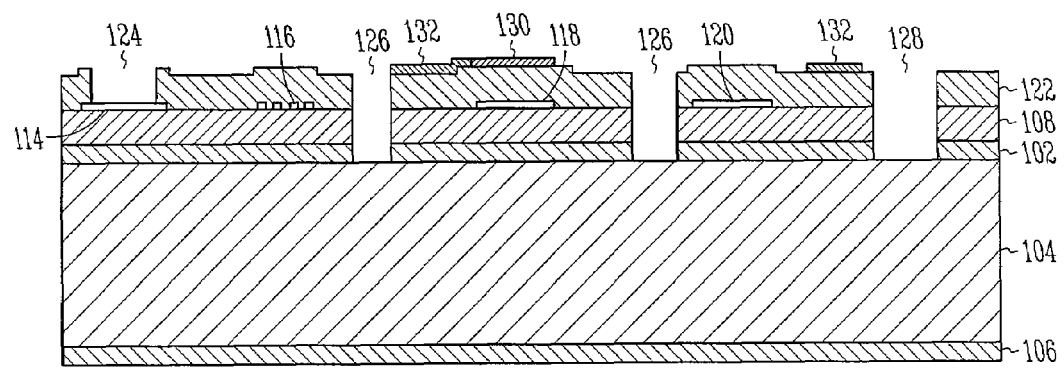
Figure 1G:
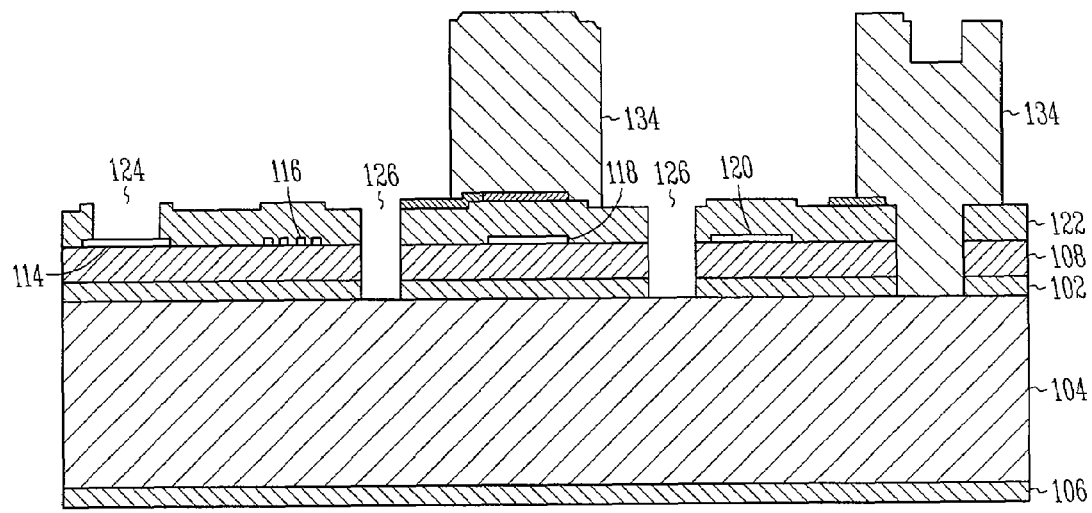
Figure 1H:
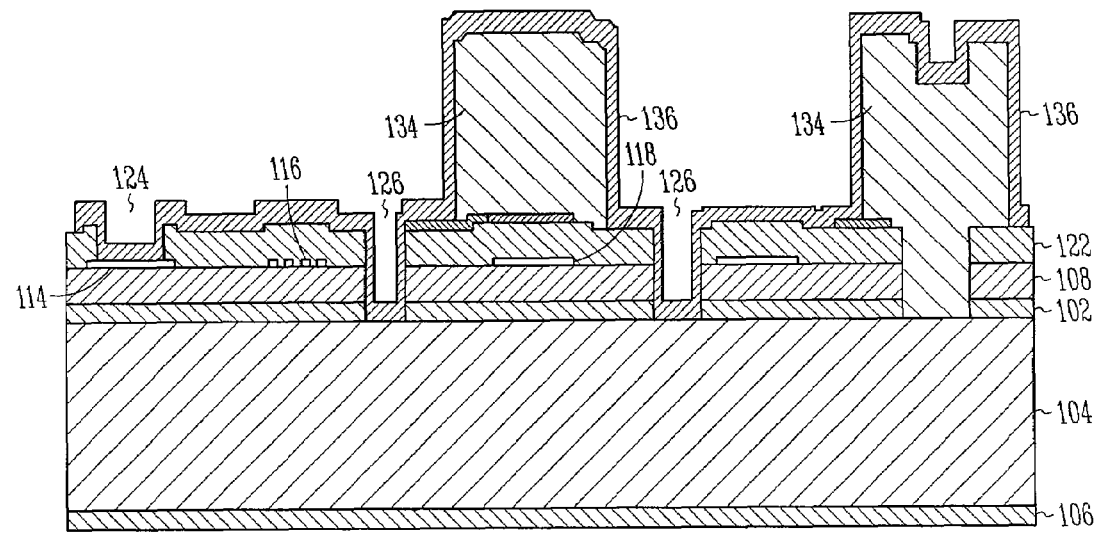
Figure 1I:
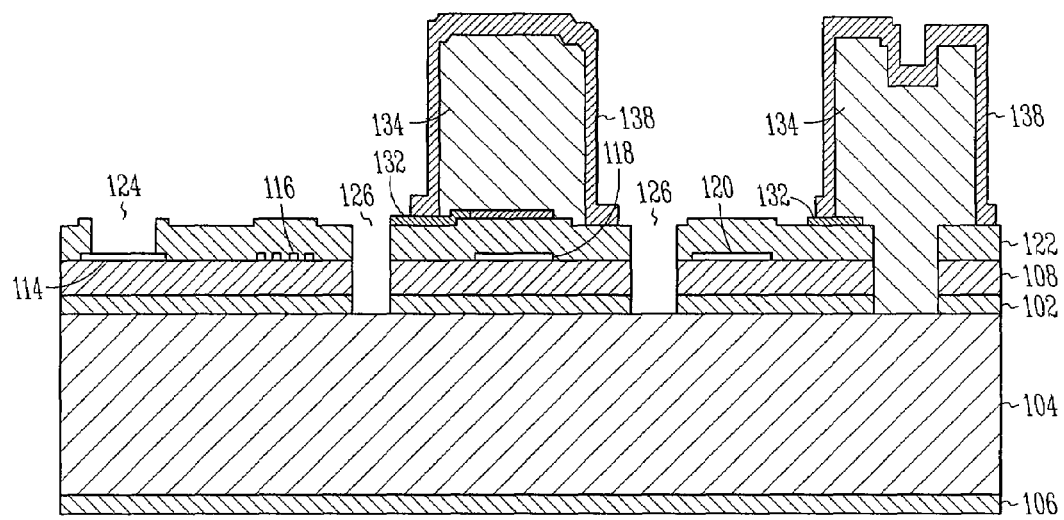
Figure 1J:
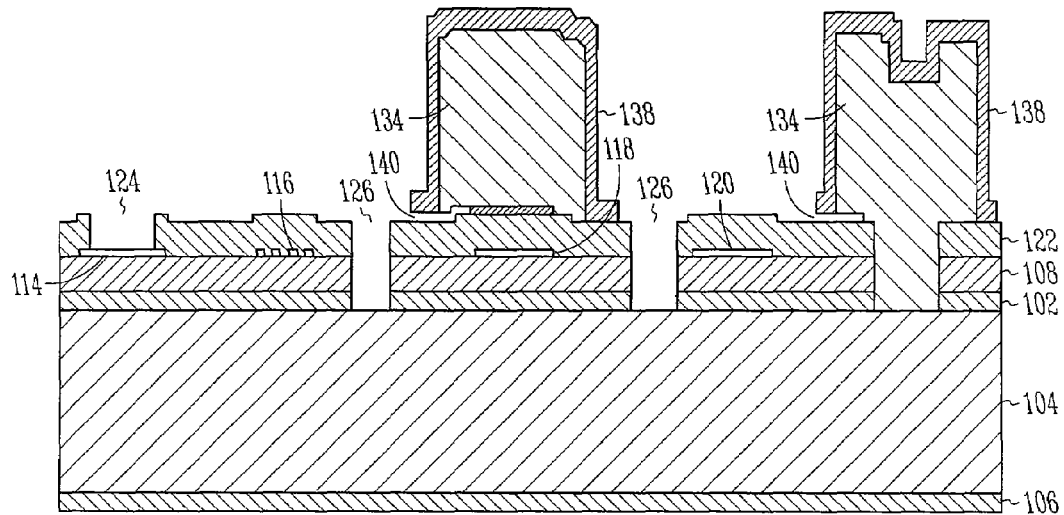
Figure 1K:
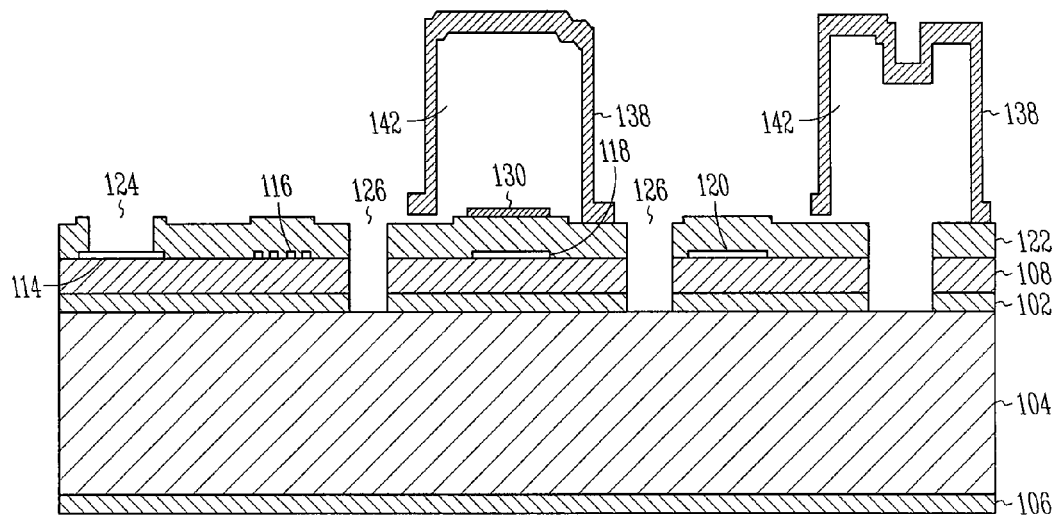
Figure 1L:
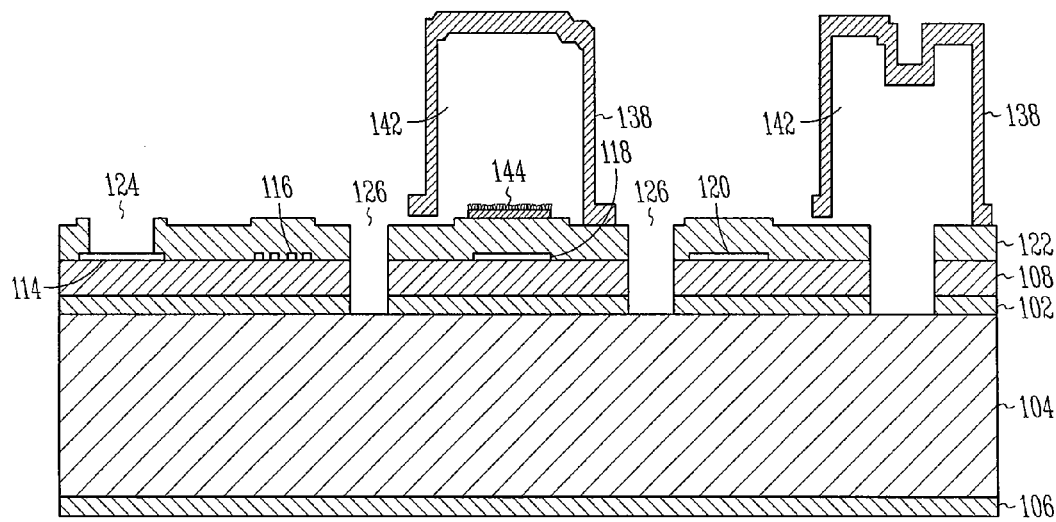
Figure 1M:
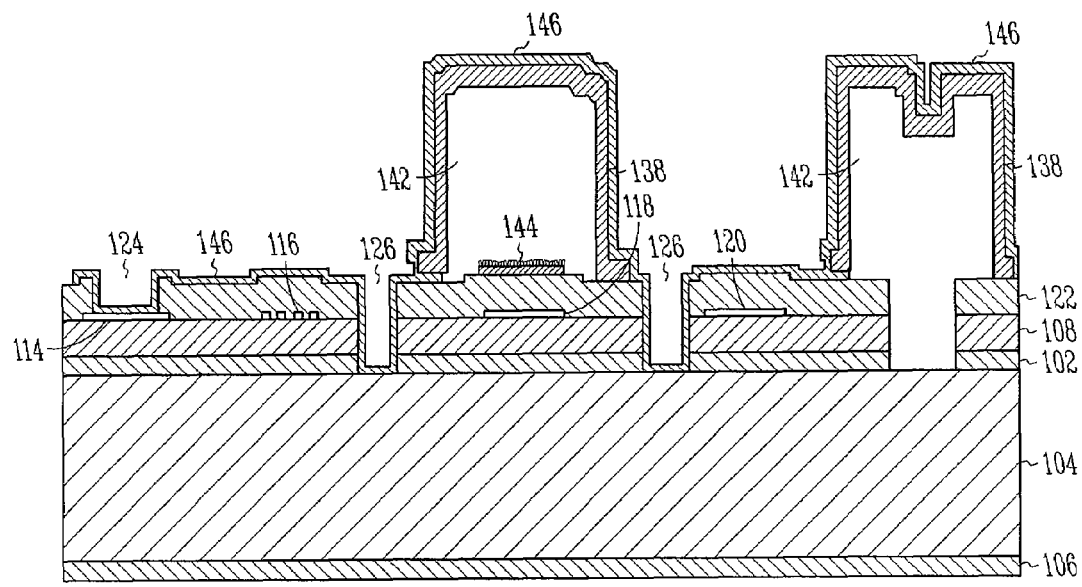
Figure 1N:
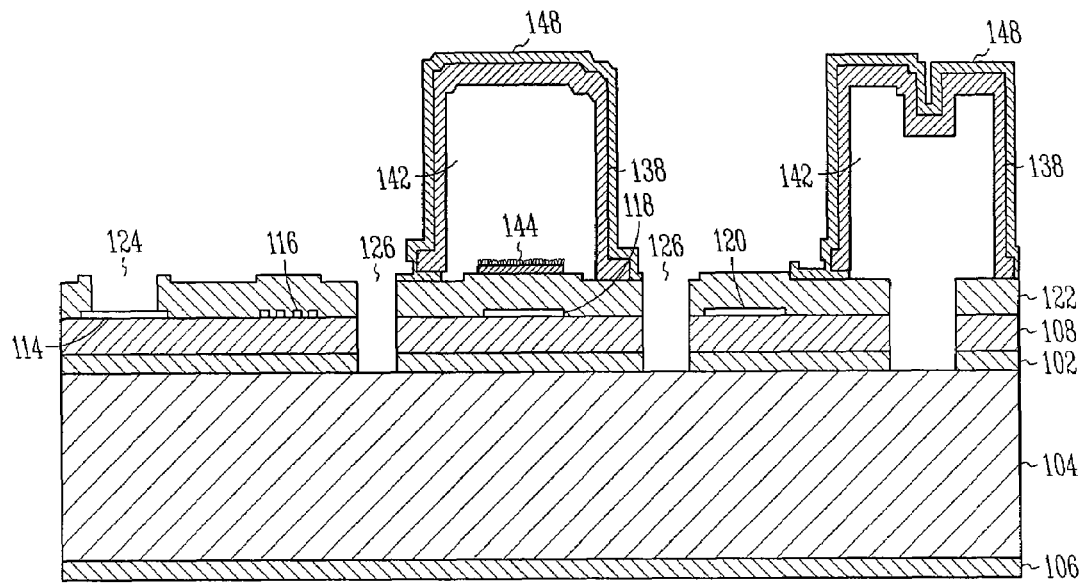
Figure 1O:
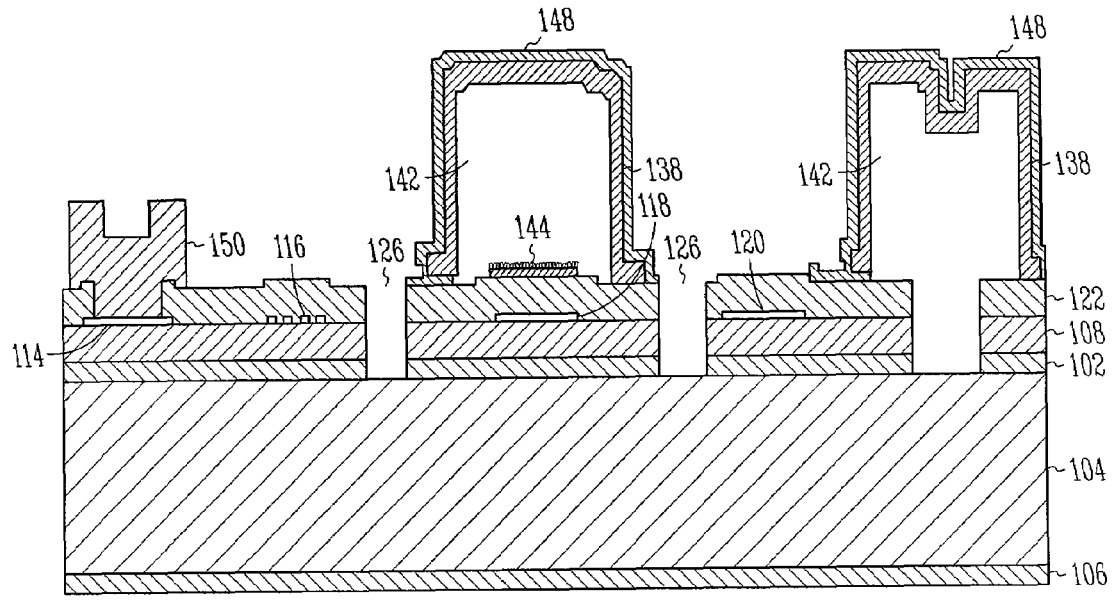
Figure 1P:
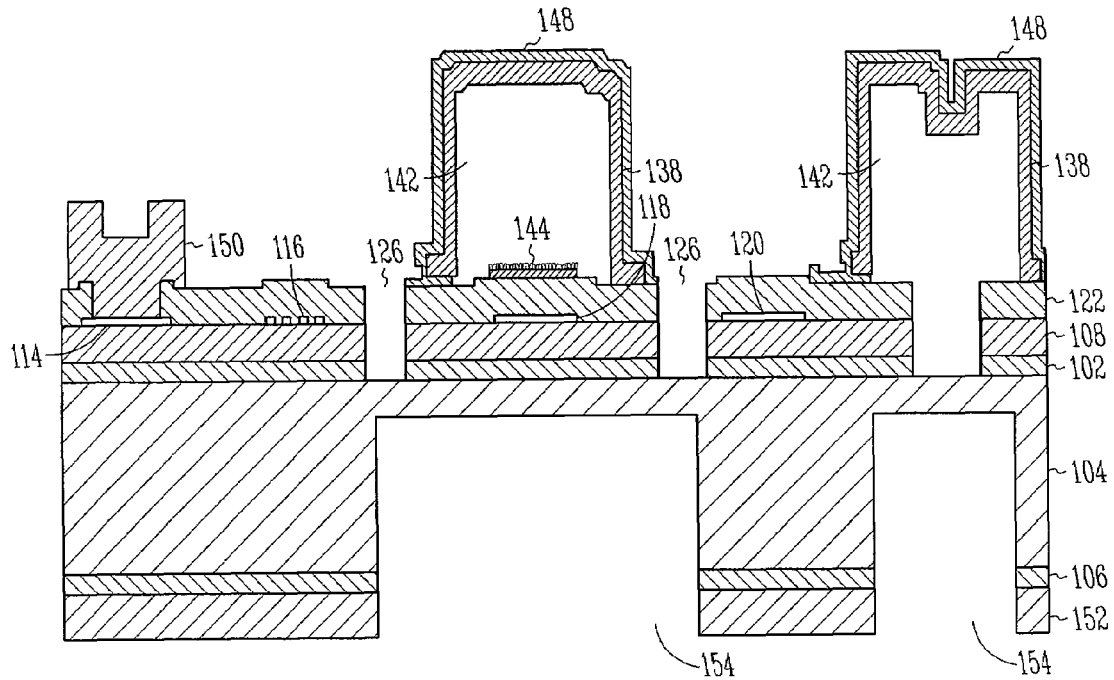
Figure 1Q:
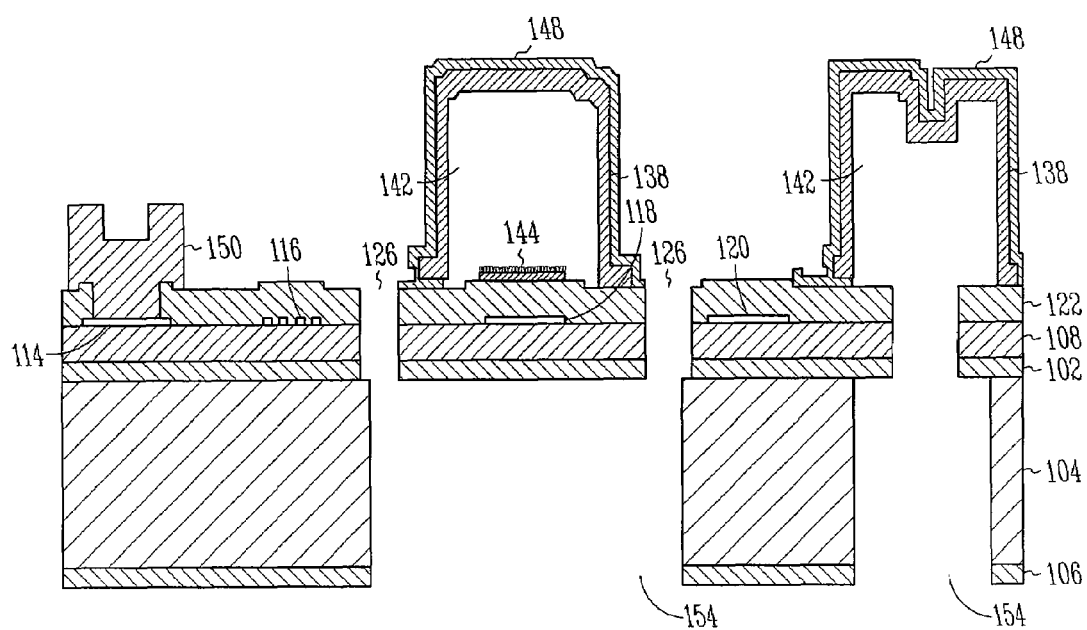
Figure 1R:
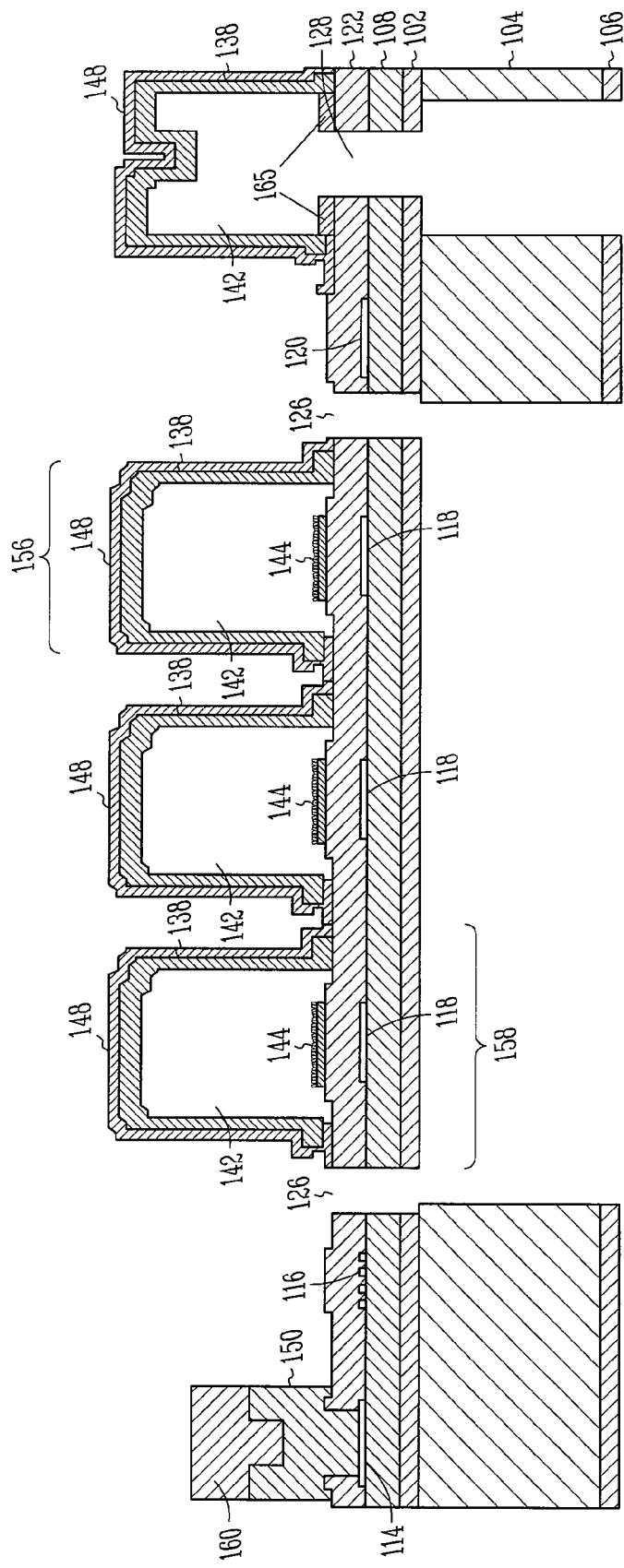

Referring to FIGS. 1A-1R, cross-sectional views of steps in a method of making a shelled thermal structure for fluid sensing are shown, according to some embodiments. A wafer 104 may be utilized as the base layer (FIG. 1A). The wafer 104 may be about 500 microns thick, for example. The wafer 104 may be between about 400 and about 600 microns thick, for example. The wafer 104 may be manufactured of silicon. The bottom silicon oxide layer 106 and top silicon oxide layer 102 surround the wafer 104. The bottom layer 106 may be about 7500 A in thickness and the top layer 102 may be about 5000 A in thickness, for example. Fluid inlet and exits 128 may be formed in the wafer, for example.

A silicon nitride layer 108 may be applied to layer 102. (FIG. 1B) A stacked layer 110 of chromium oxide, platinum and chromium oxide may next be deposited on layer 108. The chromium oxide layers assist with the poor adhesion between the nitride and platinum. A thin layer 112 of silicon nitride may then be deposited on layer 110. Photoresist may be deposited and patterned. Structures 114, 116, 118 and 120 may be etched on the wafer 104. The etching may be gas plasma etching, ion mill etching or a combination, for example. Structure 114 may be an electrical bond pad. Structure 116 may be a fine resistor or some combination of sensors, such as temperature sensors and flow sensors. Structure 118 may be a heating element. Structure 120 may be a busline, for example.

A top bridge silicon nitride layer 122 may be deposited (FIG. 1C). The deposition may be sputtering, for example. The nitride layer 122 may passivate the platinum from fluids to be analyzed and may prevent electrical leakage between surface elements. The nitride layer 122 may be a thick layer, such as about 7500 A, for example. The layer 122 may be photopatterned and etched to create contacts and vias (FIG. 1D). Inlet 128 allows for a fluid, such as gas, to move into or out of the microchip. Perforations 126 may be continuous or cut-away in multiple directions. The perforations 126 may assist in heat transfer and in supporting the analyzer structure. Via 124 allows an access to pad 114.

An adsorbing coating or catalyst 130 (FIG. 1E) may be deposited. The coating or catalyst 130 may be utilized for either a concentrator or separator, for example. The coatings and catalysts 130 are utilized to selectively interact with a fluid sample as it passes through the channel. The coating or catalyst 130 may also support carbon nanotube growth. The coatings 130 may be spun on as a film and etched to a chosen pattern, for example. The catalyst 130 may be vacuum deposited as a film by sputtering or evaporation and etched to a chosen pattern, for example.

An optional sacrificial layer 132 may be etched to form port channels (FIG. 1F). The sacrificial layer 132 may be nickel, for example. A sacrificial layer is a layer that may be later removed to release a microstructure from a substrate. A sacrificial layer may be deposited and patterned to form structures 134 (FIG. 1G). The sacrificial layer may be a polyimide or a Unity™ (Promerus LLC) polymer, for example. The structures 134 may be about 20 to about 25 microns high, for example.

A silicon dioxide layer 136 may then be deposited, such as by plasma enhance chemical vapor deposition (PECVD) or tetraethyl orthosilicate (TEOS) deposition (FIG. 1H). The silicon dioxide layer 136 may be any vapor grown glass, such as silicon nitride, for example. The layer 136 may be any type of conformal film, for example. The silicon dioxide layer 136 may be about 2 microns thick. The silicon dioxide layer 136 may then be cut away on all components except structures 134, forming layer 138 (FIG. 1I). The layer 136 may be cut away by patterning and etching. The layer 136 may also be formed by other conformal growth means or other materials, such as atomic layer deposition (ALD) of polymers or metals. The layer 136 may also be applied by some combination of ALD and PECVD or TEOS.

The ports 140 are then exposed by etching the sacrificial layer 132 (FIG. 1J). The sacrificial layer 132 may be wet etched, for example. Sacrificial layer 132 and the subsequent ports 140 formed may be utilized for removal of a polyimide sacrificial layer 134. If a Unity™ polymer is utilized, no such ports are needed. The sacrificial layer 134 may be removed through ports 140 (if a polyimide, for example) by oxygen plasma or by heating the Unity™ polymer (FIG. 1K). The Unity™ polymer will then decompose and diffuse through layer 138, with no need for ports 140. The removal allows for a fluidic channel 142 to be formed.

Optional carbon nanotubes 144 may be used as a coating and may be grown on catalyst 130 (FIG. 1L). About a 1 micron layer of silicon dioxide 146 may be deposited, such as by PECVD (FIG. 1M). This layer effectively seals the shell structures by filling ports 140 (if used with polyimide, otherwise an optional step). The silicon dioxide layer 146 may be trimmed to expose the wafer features, but the layer 148 remains on the shell structures (FIG. 1N).

One or more metal pads 150, such as a gold pad, may be shadow masked (FIG. 1O) to create an electrical contact through to the bond pad 114 and to external or integrated drive electronics 160 (see FIG. 1R). Photoresist 152 may be applied to the backside of the wafer and portions 154 etched as much as about 90% of the way through the wafer (FIG. 1P). Removal of parts of the silicon wafer 104 allows for less material to heat and increased power efficiency. The photoresist 152 may be removed and the etching completed using silicon dioxide as mask (FIG. 1Q). The etching may connect through to the perforations 126, for example. The etching may be deep reactive ion etching (DRIE), for example. The shelled thermal structures 156 may be grouped to form separators or concentrators 158 (FIG. 1R). The units 158 may be made in differing sizes to efficiently utilize heat.

One or more detectors 165 may be positioned at the both the inlet and exit of the fluidic channel, for example. The detectors may be utilized as differential detectors, such as in pairs. Detectors may also be positioned in-line, such as in the fluidic channel. Detectors may include thermal conductivity sensors or pellistors. The detectors may be implemented on the microchip or be positioned externally, for example.

Figure 2:
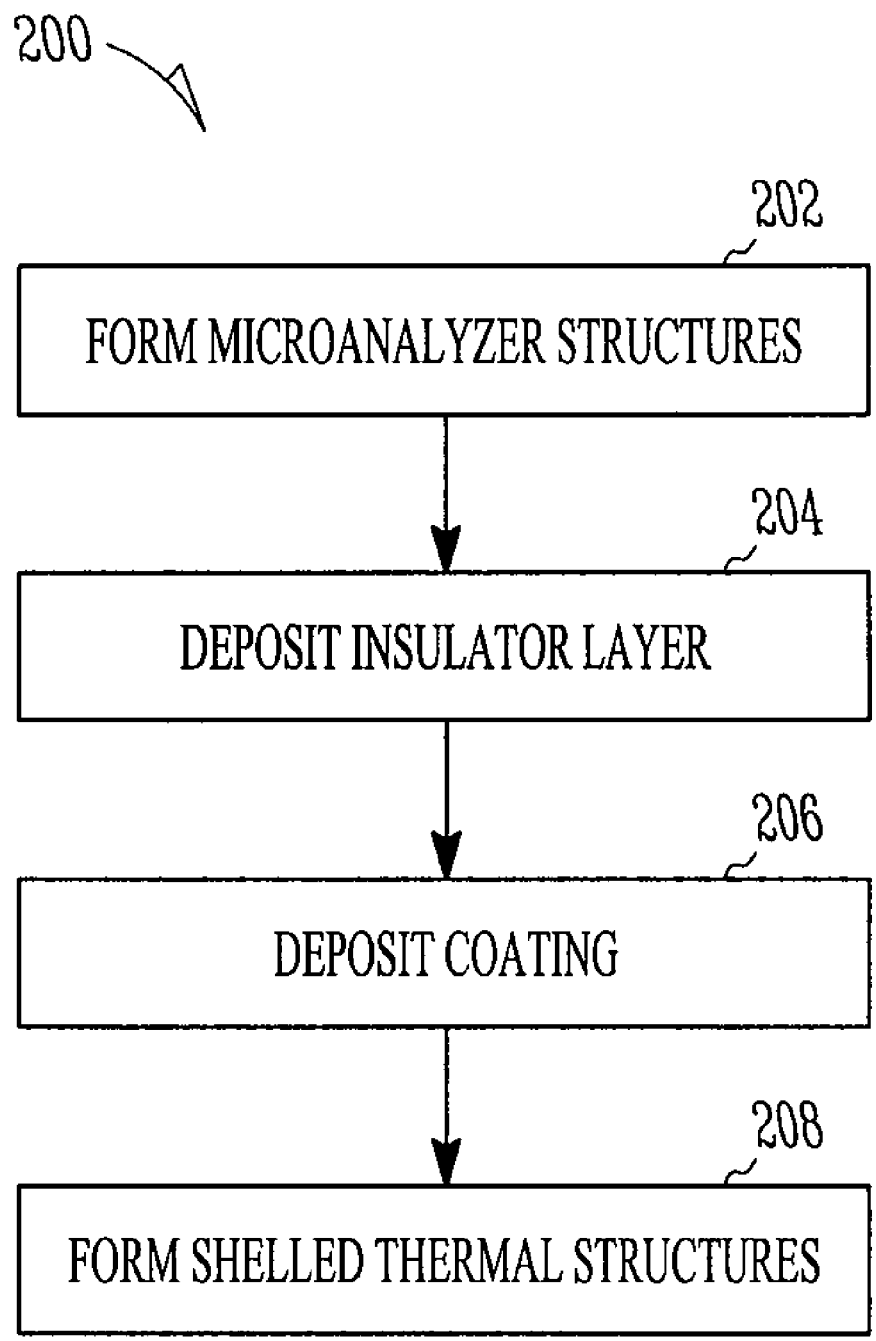
FIG. 2 illustrates a block flow diagram of a method of making a shelled thermal structure for fluid sensing, according to some embodiments.

Referring to FIG. 2, a block flow diagram of a method of making 200 a shelled thermal structure for fluid sensing is shown, according to some embodiments. Micro analyzer structures may be formed 202. Forming micro analyzer structures 202 may include depositing an insulating layer on the wafer, depositing an electrically conducting layer, depositing an insulating layer, patterning the structures, and etching.

An insulator layer may be deposited 204. Depositing 204 an insulator layer may include sputtering a nitride layer. A coating may be deposited 206.

One or more shelled thermal structures 208 may be formed. Forming 208 shelled thermal structures may include patterning and etching vias and contacts, depositing a sacrificial layer, depositing a glass layer, removing a portion of the glass layer, removing the sacrificial layer and removing a portion of the backside of the wafer. Patterning and etching vias and contacts may include photo patterning and mill ion etching. Depositing a glass layer may include vapor growing a glass layer. Depositing a glass layer includes plasma enhanced chemical vapor depositing (PECVD) silicon dioxide. Removing a portion of the glass layer includes dry etching a portion of the glass layer. Removing a portion of the backside of the wafer includes deep reactive ion etching (DRIE) a portion of the backside of the wafer.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

What is claimed is:

1. A fluidic micro analyzer, comprising:
a substrate;
drive electronics;
a thermally isolated heating layer, in electrical contact with the drive electronics and positioned on the substrate;
one or more shelled thermal structures, formed to the heating layer;
monitoring sensors, in electrical contact with the drive electronics;
a fluidic channel;
a fluid inlet, for introducing a fluidic sample to the channel;
a fluid exit; and
one or more detectors, positioned in the fluidic channel or near the fluid inlet and exit;
wherein the one or more shelled thermal structures define thee walls of at least a portion of the channel and the heating layer forms a fourth wall of at least a portion of the channel;
wherein the shelled thermal structures comprise silicon dioxide.

2. The fluidic micro analyzer of claim 1, wherein the monitoring sensors comprise one or more of temperature sensors and flow sensors.

3. A fluidic micro analyzer, comprising:
a substrate;
drive electronics;
a thermally isolated heating layer, in electrical contact with the drive electronics and positioned on the substrate;
one or more shelled thermal structures, formed to the heating layer;
monitoring sensors, in electrical contact with the drive electronics;
a fluidic channel;
a fluid inlet, for introducing a fluidic sample to the channel;
a fluid exit; and
one or more detectors, positioned in the fluidic channel or near the fluid inlet and exit;
wherein the one or more shelled thermal structures define thee walls of at least a portion of the channel and the heating layer forms a fourth wall of at least a portion of the channel;
wherein the shelled thermal structures comprise silicon nitride.

4. The fluidic micro analyzer of claim 3, wherein the monitoring sensors comprise one or more of temperature sensors and flow sensors.

* * * * *